US00PP10659P

United States Patent [19]

Mukundan et al.

[11] Patent Number: Plant 10,659

[45] Date of Patent: Oct. 20, 1998

[54] AGLAONEMA PLANT NAMED 'EMERALD STAR'

[76] Inventors: Parthasarathy Mukundan; Gopalaswamy Parthasarathy, both of "Srinivasa" 237/46 Fifth Main Road, Chamarajpet, Bangalore, India

[21] Appl. No.: 920,469

[22] Filed: Aug. 29, 1997

[51] Int. Cl.[6] ..... A01H 5/00

[52] U.S. Cl. ..... Plt./88.1

[58] Field of Search ..... Plt./88.1

[56] References Cited

U.S. PATENT DOCUMENTS

P.P. 10,247 2/1998 Brown ..... Plt./88.1

*Primary Examiner*—Howard J. Locker
*Assistant Examiner*—Kent L. Bell
*Attorney, Agent, or Firm*—C. A. Whealy

[57] ABSTRACT

A new and distinct cultivar of Aglaonema named 'Emerald Star' particularly characterized by its robust and vigorous growth rate; unique and distinct multicolored foliage pattern with prominent and persistent white, light green and dark green spots, speckles and blotches on dark green glossy leaves; numerous spots, speckles and blotches present on both leaf surfaces; notable white to whitish green midrib on upper leaf surfaces; full and dense appearance; rapid root initiation and development; good postproduction longevity; and resistance to diseases common to Aglaonema.

3 Drawing Sheets

The present invention relates to a new and distinct cultivar of Aglaonema plant, botanically known as *Aglaonema hybrida*, evaluated under the code name AG-1, and hereinafter referred to by the cultivar name 'Emerald Star'.

The new cultivar is a product of a planned breeding program conducted by the inventors in Bangalore, India. The objective of the breeding program was to create new Aglaonema cultivars having unique foliage color patterns, desirable leaf shape, compact growth habit, rapid growth rate, and resistance to diseases common to Aglaonema.

The new cultivar originated from a cross made by the inventors of an unnamed plant of *Aglaonema costatum* as the male or pollen parent with a seedling from a cross of *Aglaonema commutatum* cultivar 'Elegans' (not patented) with *Aglaonema hybrida* cultivar 'Manila' (not patented) as the female or seed parent.

The cultivar 'Emerald Star' was discovered and selected by the inventors in 1989 as a plant within the progeny of the stated cross in a controlled environment in Bangalore, India. Asexual reproduction of the new cultivar by top cuttings, stem cuttings and divisions taken in Bangalore, India, has shown that the unique features of this new Aglaonema are stable and reproduced true to type in successive generations.

The new Aglaonema has not been observed under all possible environmental conditions. The phenotype may vary somewhat with variations in environment such as temperature, light intensity and fertilizer rate, without, however, any variance in genotype.

The following traits have been repeatedly observed and are determined to be the unique characteristics of 'Emerald Star'. These characteristics in combination distinguish 'Emerald Star' as a new and distinct cultivar:

1. Plants of the new Aglaonema are very robust and vigorous.

2. Plants of the new Aglaonema have an unique and distinct multicolored foliage pattern with prominent and persistent white, light green and dark green spots, speckles and blotches on dark green glossy leaves. Numerous spots, speckles and blotches are present on both leaf surfaces.

3. The upper surface of leaves of the new Aglaonema have a notable white to whitish green midrib.

4. Plants of the new Aglaonema produce divisions readily and leaves are closely spaced giving plants a full and dense appearance.

5. Plants of the new Aglaonema initiate and develop roots rapidly.

6. Plants of the new Aglaonema have good postproduction longevity as plants are very tolerant of low light conditions.

7. Plants of the new Aglaonema are exceptionally resistant to diseases common to Aglaonema.

Plants of the new Aglaonema can be compared to the *Aglaonema hybrida* cultivar 'Stars' (disclosed in U.S. Plant Pat. No. 10,247). However in side-by-side comparisions conducted in Bangalore, India, Zolfo Springs, Fla., and Miami, Fla., plants of the new Aglaonema differ from plants of the cultivar 'Stars' in the following characteristics:

1. Plants of the new Aglaonema are more spreading, taller, fuller and denser than plants of the cultivar 'Stars'.

2. Leaves of plants of the new Aglaonema are more numerous, thicker, narrower, longer, more erect, and more undulating than leaves of plants of the cultivar 'Stars'.

3. Leaves of the new Aglaonema are darker green and more intensely spotted, speckled and blotched than leaves of the cultivar 'Stars'.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The first sheet of photographs comprises a side perspective view (top photograph) and a top perspective view (bottom photograph) of a typical single plant of 'Emerald Star'.

The second sheet of photographs comprises a close-up view of the upper surface of a fully-expanded leaf (top photograph) and a close-up view of the lower surfaces of fully-expanded leaves (bottom photograph).

The third sheet comprises a comparison view of the cultivars 'Stars' (left) and 'Emerald Star' (right). Leaf colors in the photographs may appear different from the actual colors due to light reflectance.

DETAILED BOTANICAL DESCRIPTION

The following observations, measurements and comparisons describe plants grown in Zolfo Springs, Fla., under a polypropylene-covered shadehouse and conditions which closely approximate those used in horticultural practice. Plants were grown under day temperatures ranging from 21° to 38° C. and night temperatures ranging from 7° to 21° C. The polypropylene shade provided a 84 percent decrease in ambient light levels.

In the following description, color references are made to The Royal Horticultural Society Colour Chart except where general terms of ordinary dictionary significance are used.

Botanical classification: *Aglaonema hybrida* cultivar 'Emerald Star'.

Parentage:

*Male parent.*—An unnamed plant of *Aglaonema costatum.*

*Female parent.*—Seedling from a cross of *Aglaonema commutatum* cultivar 'Elegans' with *Aglaonema hybrida* cultivar 'Manila'.

Propagation:

*Method.*—By top cuttings, stem cuttings and by division.

*Time to initiate roots.*—Summer: About 14 days at 27° to 35° C. Winter: About 20 days to 20° to 25° C.

*Time to develop roots.*—Summer: About 21 days at 27° to 35° C. Winter: 30 to 35 days at 20° to 25° C.

*Root description.*—Thick, fibrous, fleshy, and white in color.

Plant description:

*Plant shape.*—Upright and somewhat outwardly spreading, inverted triangle, symmetrical. Closely-spaced numerous leaves and divisions give plants a full, dense appearance.

*Growth habit.*—Erect when young, becoming more outwardly arching and spreading as leaves develop. Appropriate for 14 to 20-cm containers.

*Plant size.*—Height, soil surface to top of leaf canopy: About 45 cm. Width: About 55 cm.

*Plant vigor.*—Vigorous, rapid growth rate.

*Foliage description.*—Leaf shape: Young: Linear to lanceolate. Fully-expanded: Lanceolate. Leaf length, fully expanded: About 28 cm. Leaf width, fully expanded: About 8.25 cm. Margin: Entire. Leaf surface: Flat, undulating. Leaf tip: Acuminate. Leaf base: Obtuse. Leaf aspect: Erect initially, eventually mature leaves held horizontal to the stem. Leaf texture: Leathery, smooth, glabrous. Leaf color: Young, upper surface: Background: Close to 147B, glossy. Random spots, speckles and blotches: Dark green, 147A, and darker than 147A; and light green, 154A/154B. Margin: Darker than 147A. Young, lower surface: Background: Greener than 146A, dull. Random spots, speckles and blotches: White, 155D. Mature, upper surface: Background: Close to 147A, glossy. Random spots, speckles and blotches: Dark green, much darker than 147A; light green, 154A/154B; and white, 155D. Margin: Darker than 147A. Mature, lower surface: Background: Close to 146A, dull. Random spots, speckles and blotches: White, 155D. Petiole length, primary shoot: About 8 cm. Petiole diameter, primary shoot, at leaf base: About 5 mm. Petiole diameter, primary shoot, at stem: About 1 cm. Petiole wing: Length: About 6 cm. Width: About 6 mm. Petiole color: Young: 147A with random white spots. Mature: Distal: 147A with random white spots. Proximal: 144A to 147A. Venation: Upper surface: Sunken, laterals same color as leaf color, midvein white to whitish green. Lower surface: Prominent, laterals same color as leaf, midvein, 144A.

*Inflorescence.*—Typical of Aglaonema, no commercial significance.

Disease tolerance: Plants of the new Aglaonema are exceptionally resistant to diseases common to Aglaonema.

It is claimed:

1. A new and distinct cultivar of Aglaonema plant named 'Emerald Star', as illustrated and described.

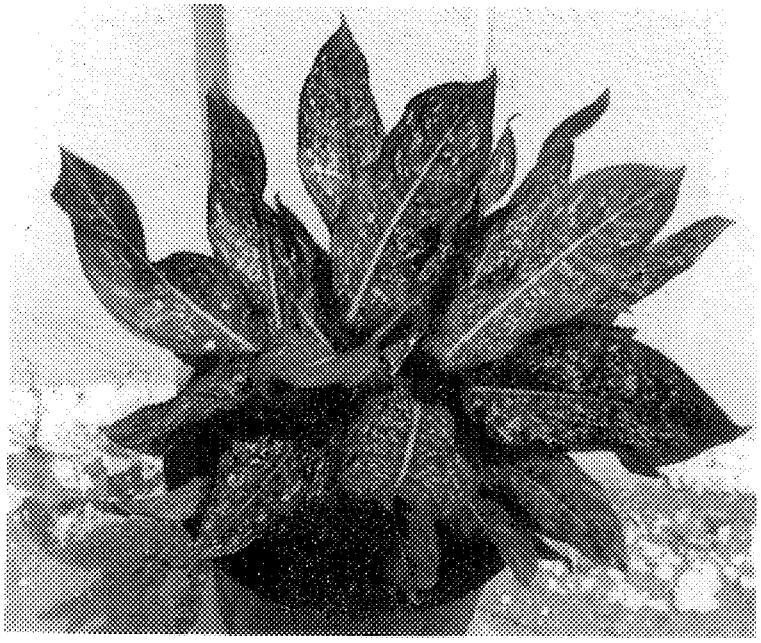
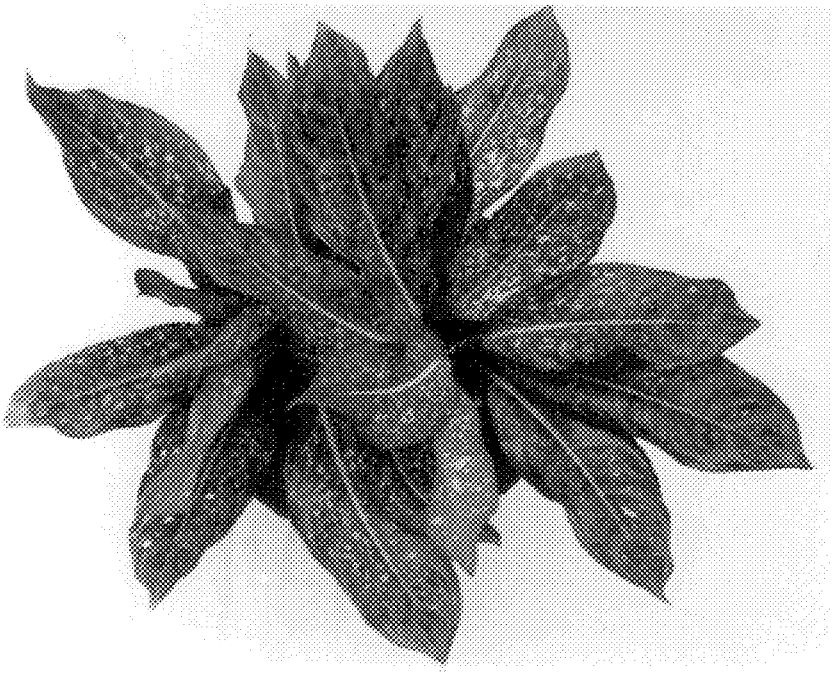

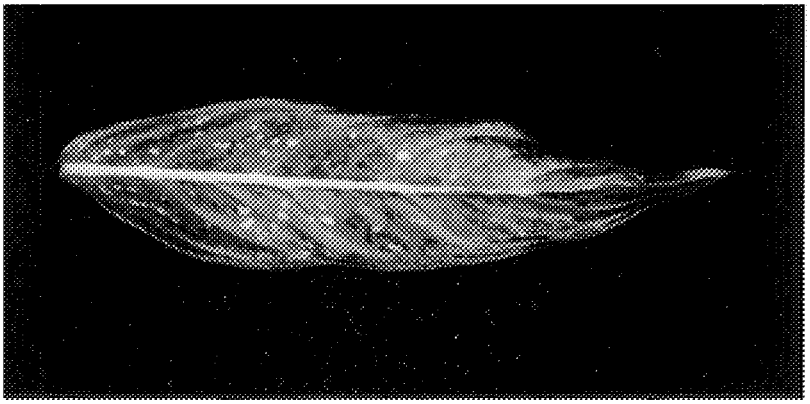
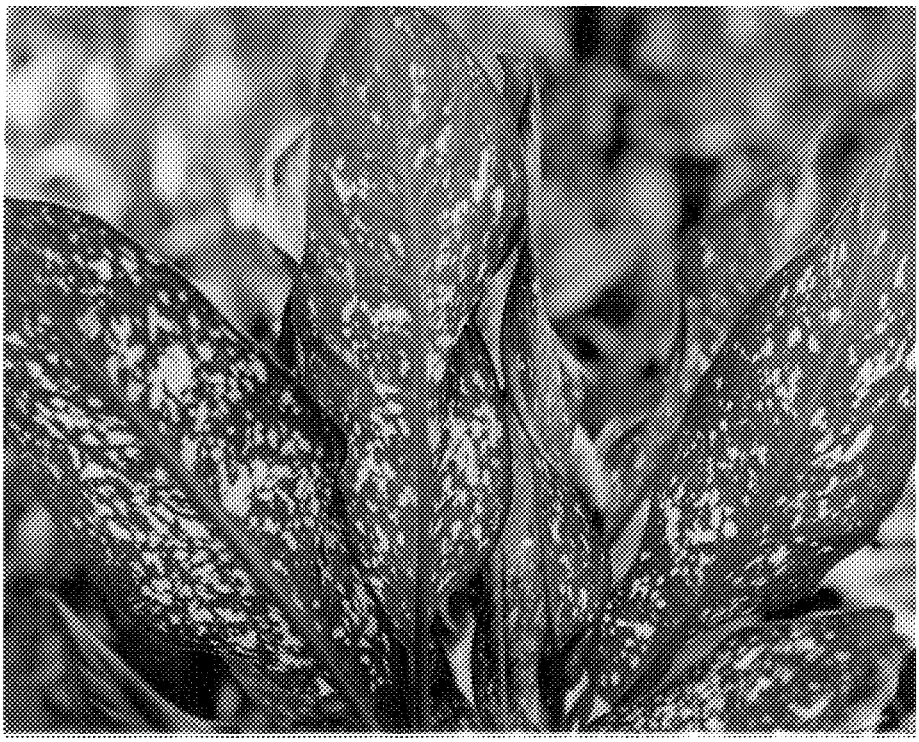

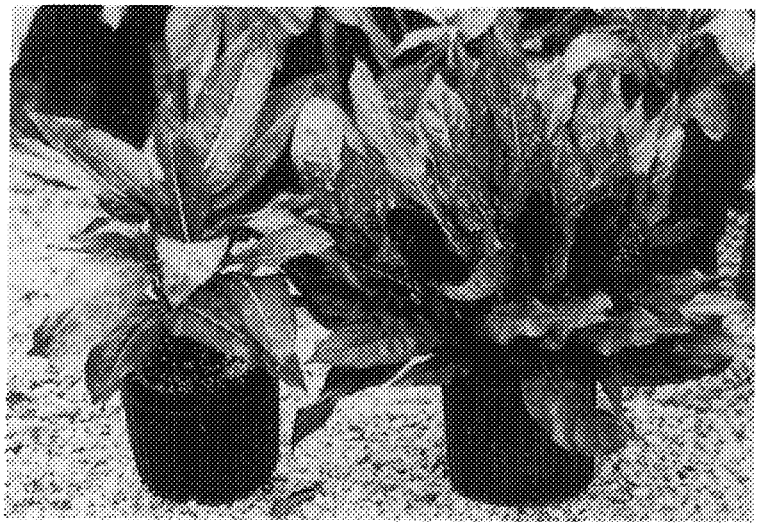

* * * * *